US008600132B2

(12) United States Patent
Razifar et al.

(10) Patent No.: US 8,600,132 B2
(45) Date of Patent: Dec. 3, 2013

(54) METHOD AND APPARATUS FOR MOTION CORRECTING MEDICAL IMAGES

(75) Inventors: Pasha Razifar, Uppsala (SE); Kris Filip Johan Jules Thielemans, Putney (GB); Shailendra Rathore, Woodford Green (GB)

(73) Assignee: General Electric Company, Schenectady, NY (US)

( * ) Notice: Subject to any disclaimer, the term of this patent is extended or adjusted under 35 U.S.C. 154(b) by 415 days.

(21) Appl. No.: 13/099,558

(22) Filed: May 3, 2011

(65) Prior Publication Data

US 2012/0281897 A1  Nov. 8, 2012

(51) Int. Cl.
*G06K 9/00* (2006.01)
(52) U.S. Cl.
USPC ............ 382/128; 382/131; 382/132; 382/154
(58) Field of Classification Search
USPC .................................. 382/128, 131, 132, 154
See application file for complete search history.

(56) References Cited

U.S. PATENT DOCUMENTS

| | | | | |
|---|---|---|---|---|
| 5,983,251 | A * | 11/1999 | Martens et al. | 708/203 |
| 7,136,518 | B2 * | 11/2006 | Griffin et al. | 382/133 |
| 7,831,088 | B2 * | 11/2010 | Frakes et al. | 382/154 |
| 8,175,360 | B2 * | 5/2012 | Razifar et al. | 382/131 |
| 8,233,689 | B2 * | 7/2012 | Razifar et al. | 382/131 |
| 2010/0135556 | A1 | 6/2010 | Razifar et al. | |

OTHER PUBLICATIONS

E.D. Brandner et al., "Abdominal organ motion measured using 4D CT", Int. J. Radiat. Oncol., Biol., Phys. 65(2), 554-560, 2006.
P.E. Kinahan et all; "Attenuation Correction for a combined 3D PET/CT Scanner", Med. Phys. 25(10), 2046-2053, 1998.
P Razifar et al; "Volume-Wise Application of Principal Component Analysis on Masked Dynamic PET Data in Sinogram Domain". IEEE Trans. Nucl. Sc. 53, 2759-68, 2006.
M. M. Osman et al.; "Clinically significant inaccurate localization of lesions with PET/CT: Frequency in 300 patients", J. Nucl. Med. Technol. 44, 240-243, 2005.
Y.E. Erdi et al., "PET-CT: The CT motion quantitation of lung lesions and its impact on PET-measured SUVs", J. Nucl. Med. Technol. 45, 1287-1292, 2004.
M. Dawood et al; "Respiratory Gating in positron emission tomography: A quantitive comparisioin of different gating schemes", Med. Phys. 34(7), 2007.
P. Razifar et al; "Principal Component Analysis with Pre-Normalization Improves the Signal-to-Noise Ratio and Image Quality in Positron Emission Tomography Studies of Amyloid Deposits in Alzheimer's Disease" Phys. Med. Biol. (54) 2009, 3595-3612.

* cited by examiner

*Primary Examiner* — Tom Y Lu
(74) *Attorney, Agent, or Firm* — The Small Patent Law Group; Dean D. Small (57) ABSTRACT

A method for reducing, in an image, motion related imaging artifacts includes obtaining an image dataset of a region of interest, generating a plurality of intermediate images using the image dataset, applying a multivariate data analysis technique to the plurality of the intermediate images to generate motion information, sorting the intermediate images into a plurality of bins based on the motion information, and generating an image of the region of interest using at least one of the plurality of bins.

20 Claims, 11 Drawing Sheets

METHOD AND APPARATUS FOR MOTION CORRECTING MEDICAL IMAGES

BACKGROUND OF THE INVENTION

The subject matter disclosed herein relates generally to imaging systems, and more particularly to an apparatus and method for motion-correcting medical images.

Multi-modality imaging systems exist that scan using different modalities, for example, Computed Tomography (CT), Magnetic Resonance Imaging (MRI), Positron Emission Tomography (PET), and Single Photon Emission Computed Tomography (SPECT). During operation, the image quality of the conventional imaging systems may be affected by the motion of the object being imaged. In particular, motion of the imaged object can degrade the image quality. More specifically, image artifacts are produced by movement of the object during image acquisition. Respiratory motion is a common source of involuntary motion in mammals (e.g., people and animals) encountered in medical imaging systems. The respiratory motion may lead to errors during image review, such as when a physician is determining the size of a lesion, determining the location of the lesion, or quantifying the lesion.

Moreover, in multi-modality systems, for example, an integrated PET/CT system, the PET and CT images should be registered with one another. However, since the CT images are typically acquired during a short time period, the attenuation map generated by the CT images represents the attenuation characteristics of the patient during full exhalation where there is no breathing motion. In contrast, the PET images are typically acquired over a relatively long time period where a patient is allowed to breathe freely due to the long acquisition time. The mismatch between the two data acquisition modes may result in image artifacts in the attenuation corrected PET images.

One known method for reducing the imaging artifacts is to average the CT image (or the maximum intensity CT image) of multiple respiratory phases to mimic the effect of the PET acquisition collected over multiple respiratory cycles. Another known method for reducing the imaging artifacts is to use respiratory gated CT acquisitions to generate attenuation correction maps that better match the respiratory characteristics of the respiratory gated PET acquisition. A further method may include requesting the patient to hold his breath during the scan. However, because PET data may be acquired over several minutes, the patient typically has to breath several times during the PET acquisition, resulting in image artifacts

BRIEF DESCRIPTION OF THE INVENTION

In one embodiment, a method for reducing, in an image, motion related imaging artifacts is provided. The method includes obtaining an image dataset of a region of interest, applying a multivariate data analysis technique to the image dataset to generate motion information, sorting the image dataset into a plurality of bins based on the motion information, and generating an image of the region of interest using at least one of the plurality of bins.

In another embodiment, a medical imaging system including a scanner and a computer operationally coupled to the scanner is provided. The computer is programmed to acquire an imaging dataset of an object using the scanner, generate a plurality of intermediate images using the image dataset, apply a multivariate data analysis technique to the plurality of intermediate images to generate motion information, sort the intermediate images into a plurality of bins based on the motion information, and generate an image of the region of interest using at least one of the plurality of bins.

In a further embodiment, a non-transitory computer readable medium is provided. The computer readable medium is encoded with a program programmed to instruct a computer is provided. To acquire an imaging dataset of an object using the scanner, generate a plurality of intermediate images using the image dataset, apply a multivariate data analysis technique to the plurality of intermediate images to generate motion information, sort the intermediate images into a plurality of bins based on the motion information, and generate an image of the region of interest using at least one of the plurality of bins.

DETAILED DESCRIPTION OF THE INVENTION

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Figure 1:
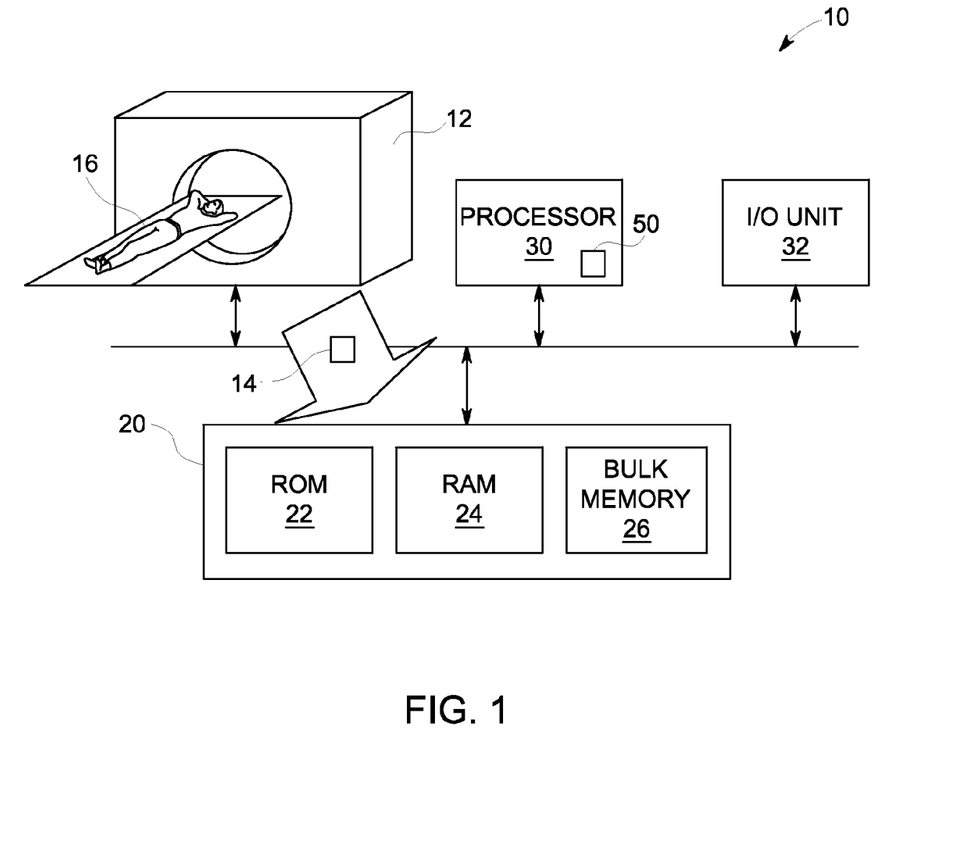
FIG. 1 is a simplified schematic illustration of an exemplary imaging system formed in accordance with various embodiments.

FIG. 1 is a simplified block diagram that illustrates an exemplary Positron Emission Tomography (PET) imaging system 10. The PET imaging system 10 may include a PET scanner 12 that is operable to generate a four-dimensional (4D) emission dataset 14 of a patient 16. The 4D emission dataset 14 represents three spatial dimensions and time. The 4D emission dataset 14 may be stored in a memory device 20. The memory device 20 may include any combination of memory circuits, including electrical, magnetic, and/or optical systems. The memory device 20 may include, for example, a read only memory (ROM) 22, a random access memory (RAM) 24, and/or a bulk memory 26.

The memory device 20 may have stored therein program instructions to be executed by a processor 30. The program instructions may be written in any suitable appropriate computer language, e.g., Matlab. The processor 30 may be any one or combination of suitably appropriate processing systems, such as, for example, a microprocessor, a digital signal processor, and a field programmable logic array, among others. The processing system may be embodied as any suitably appropriate computing device, e.g., a computer, personal digital assistant (PDA), laptop computer, notebook computer, a hard-drive based device, or any device that can receive, send, and store data. An input/output (I/O) device 32 may be provided for receiving user inputs and/or for providing outputs to a user. The I/O device 32 may also be a communication link which enables data to be transferred to and/or from other devices, e.g., over a network. The I/O device 32 may include a display device (not shown) for displaying a PET image. The I/O device 32 may include a device for receiving input from the user. For example, the device may include a mouse, trackball, or touch sensitive interface. The imaging system 10 also includes a motion characterization module 50 that is adapted to identify motion within the emission dataset 14 and utilize the identified motion to partition the emission dataset 14 into a plurality of bins, wherein at least one of the bins is then used to reconstruct at least one image of the patient 16 as is discussed in more detail below. In the exemplary embodiment, the emission dataset 14 is a 4D emission dataset and the motion characterization module is installed in the processor 30. The motion characterization module may be implemented as a hardware device, as software, or a combination thereof.

Figure 2:
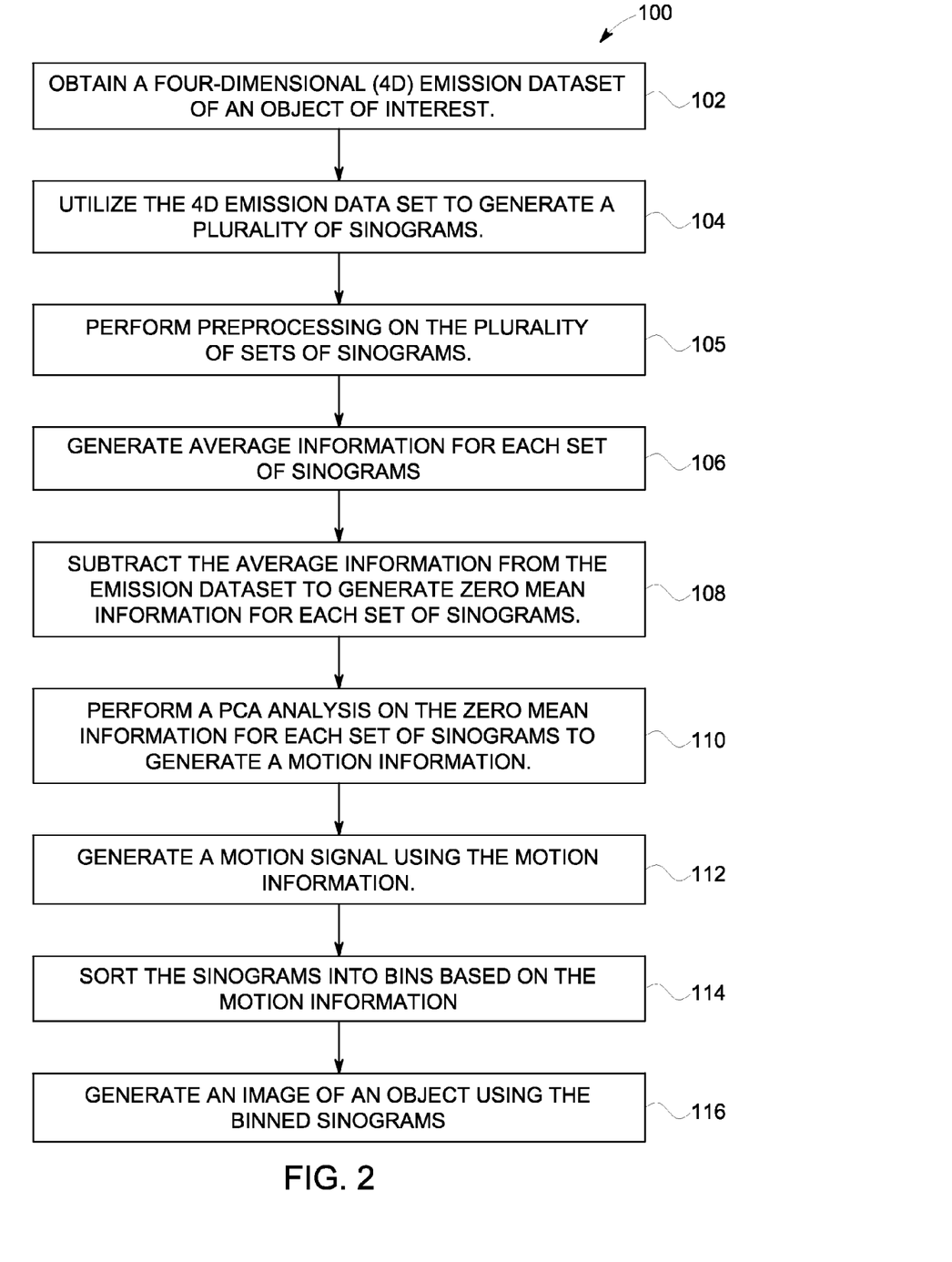
FIG. 2 is a flowchart illustrating a method for reducing motion related imaging artifacts in accordance with various embodiments.

FIG. 2 is a block diagram of an exemplary method performed by the PET imaging system 10 shown in FIG. 1. In the exemplary embodiment, the method 100 may be implemented using the motion characterization module 50. More specifically, the method 100 may be provided as a machine-readable medium or media having instructions recorded thereon for directing the processor 30 to perform an embodiment of the method described herein. The medium or media may be any type of CD-ROM, DVD, floppy disk, hard disk, optical disk, flash RAM drive, or other type of computer-readable medium or a combination thereof.

The method 100 provides motion characterization, or motion reduction, on the emission dataset 14 to account for the motion of the object 16. In operation, the method 100 identifies the motion of the object 16 and re-organizes the emission dataset 14 to enable an image of the object 16 to be reconstructed. It should be realized that although the method 100 is described with respect to the emission dataset 14 obtained from the PET imaging system 10, the method 100 may also be applied to a transmission dataset obtained from a CT imaging system. Moreover, the method 100 may be applied to any image dataset or sinogram data obtained using any of the imaging modalities discussed herein, and the emission dataset 14 is exemplary only.

At 102, the emission dataset 14 of the object 16 (each shown in FIG. 1) is obtained. In the exemplary embodiment, the emission dataset 14 is obtained using the PET imaging system 10 (shown in FIG. 1). The emission dataset 14 may be obtained by performing an emission scan of the object 16 to produce the emission dataset 14. Optionally, the emission dataset 14 may be obtained from data collected during a previous scan of the object 16, wherein the emission dataset 14 has been stored in a memory, such as the memory device 20 (shown in FIG. 1). The emission dataset 14 may be stored in any format, such as a list mode dataset, for example. The emission dataset 14 may be obtained during real-time scanning of the patient 16. For example, the methods described herein may be performed on emission data as the emission data is received from the PET scanner 12 during a real-time examination of the patient 16.

Figure 3:
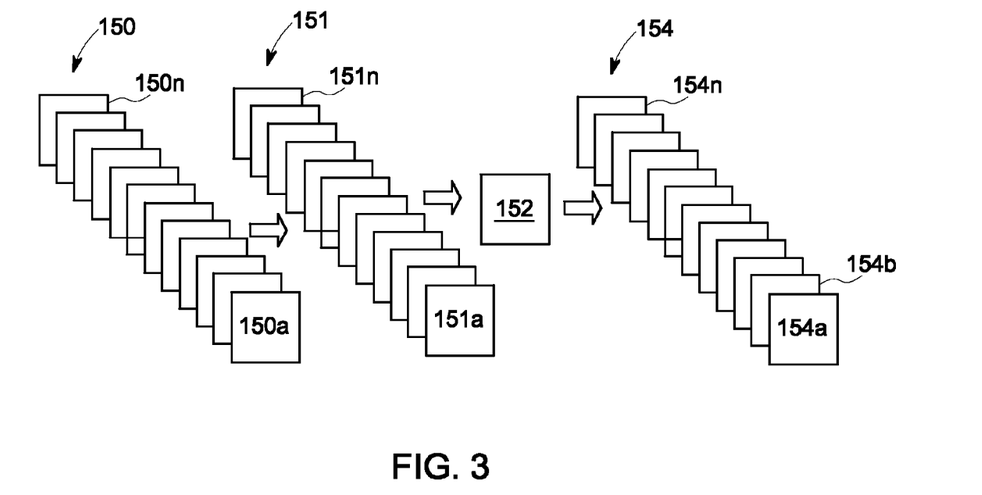
FIG. 3 is a simplified block diagram illustrating exemplary sinograms formed in accordance with various embodiments.

At 104, the emission dataset 14 is utilized to generate a plurality of intermediate images 150 over time. In the exemplary embodiment, the intermediate images 150 are sinograms 150. Optionally, the intermediate images may be reconstructed images. As shown in FIG. 3, the plurality of sinograms 150 may include a first set of sinograms 150a, acquired over a first time frame of, for example, 300 milliseconds. The plurality of sinograms 150 may include a second set of sinograms 150b that are acquired over a time frame subsequent to the first set of sinograms 150a, etc. Thus, a set of sinograms is generated for each time frame, e.g. for each 300 ms time frame, during the scanning process. The number of sinograms 150 generated is based on the number of detectors installed in the imaging system 10, the speed of the expected motion, the length of the scan performed at 102, etc. Thus, the plurality of sinograms 150 may include multiple sets of sinograms (150a . . . 150n) acquired over consecutive time frames in the scanning process, e.g. a single set of sinograms may be acquired for each 300 milliseconds over the entire scan process. The sinograms 150 may be generated by operating the system 10 in a sinogram mode. Sinogram mode generally refers to an acquisition mode in which annihilation events, optionally having an identical Time-of-Flight (TOF), are stored in sinograms in an (radius from axis, angle) format. The array of responses is known as a sinogram. It should be realized that other methods and/or devices may be used for data storage and that the sinograms described herein represent one such exemplary method of storing data.

At 105, the sinograms 150 generated at 104 are preprocessed to obtain a corresponding set 151. For example, the sinograms 150 may be preprocessed by 1) averaging over different elements of the sinograms (i.e. data-size and noise reduction) 2) removal of certain elements of the sinograms (e.g. by applying a mask where motion is expected to occur, or where the patient data contributes high spatial information, e.g. excluding regions with only accidental or scattered coincidences) 3) correction for known changes over time (e.g. due to radioactive decay) 4) applying an element-wise operation on the data to convert data to approximately Gaussian distributed, preferably with uniform variance. For example, for data that is Poisson distributed, appropriate transformations include the Anscombe transformation, the Freeman-Tukey transformation, or simply taking the square root. Both averaging and masking may rely on external information, e.g. a previous scan, and/or prior knowledge about main direction and location of motion. For example, the patient outline or a region of interest such as the diaphragm could be determined from the images obtained from a previous CT scan. This region information can then be transformed to sinograms using a model of the PET scanner. The mask can also be derived from the average data itself (e.g. detect background counts based on a threshold)

At 106, the sets of pre-processed sinograms 151a . . . 151n are utilized to generate time-average information 152. For example, assuming that twenty-five sets of sinograms 150a . . . 150n are generated at 104 for each time frame, then at 105, twenty-five preprocessed sinograms 151a . . . 151n are generated, and at 106, average information 152 is generated for every element in every sinogram in 150a, computing the average of the 25 corresponding elements.

Figure 4:
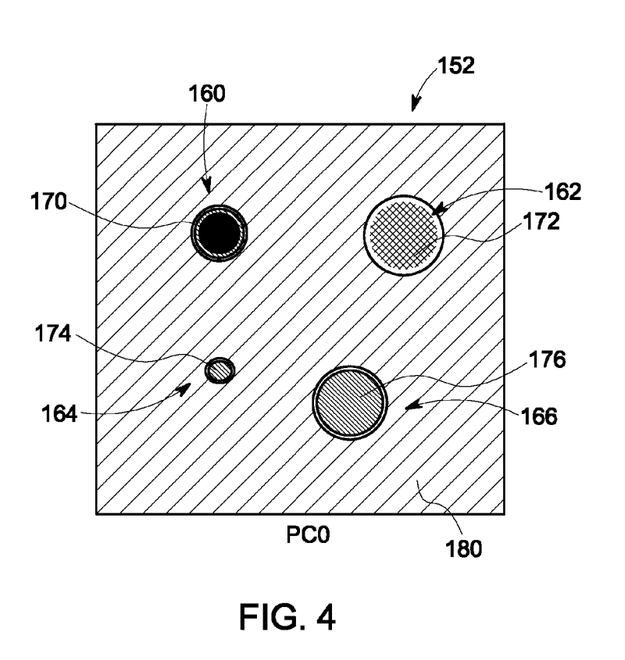
FIG. 4 is an exemplary image representing average information that may be generated in accordance with various embodiments.

FIG. 4 illustrates exemplary average information 152 that may be generated from the set of sinograms 151a . . . 151n. The visual representation of the average information generated for the set of sinograms 151a . . . 151n is denoted as PC0 in FIG. 4. The average information 152 is acquired by determining the average information (over time) for each set of preprocessed sinograms 150 as discussed above. For example, FIG. 4, e.g. PC0, illustrates average information acquired by scanning four exemplary uniform objects 160, 162, 164, and 166 where in this case the motion of each of the four objects was in vertical direction. As shown in FIG. 4, the four objects 160, 162, 164, and 166 each exhibit a change in the average pixel intensity near the outer edge of each object. Moreover, the inner regions 170, 172, 174, and 176 of each object 160, 162, 164, and 166, respectively, and the surrounding background area 180 is substantially solid indicating that there is little or no deviation in the pixel intensity over time.

At 108, the average information 152, for each set of sinograms 151a . . . 151n, is subtracted from the respective set of sinograms 150 to generate zero mean information which is then input to the PCA. Accordingly, assuming that there are 25 sets of sinograms 150 generated over time during an exemplary scan, the method includes generating average information 152 for each of the 25 sets of sinograms 150 and then generating zero mean information 154 for each of the 25 sets of sinograms 150.

Figure 5:
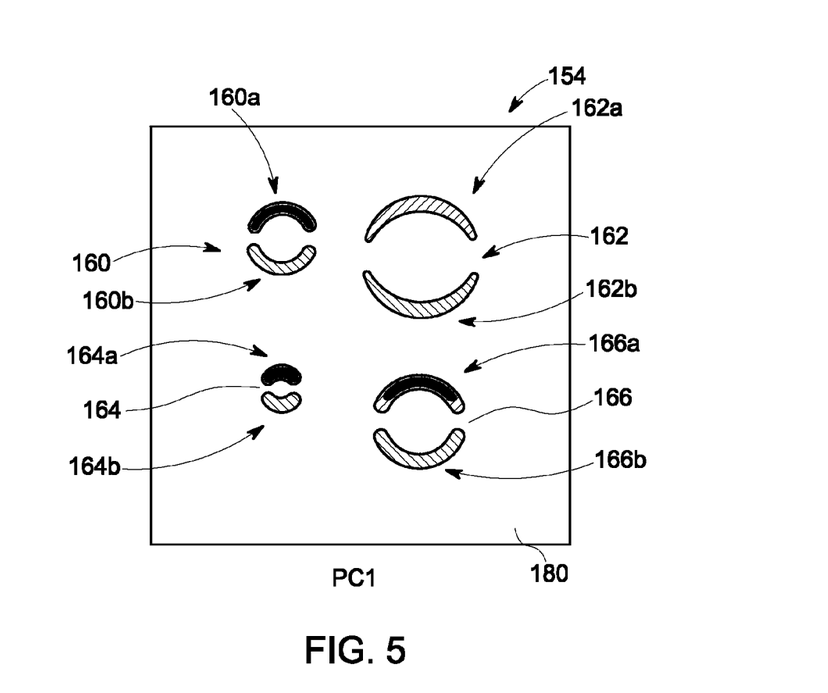
FIG. 5 is an exemplary image representing motion information that may be generated in accordance with various embodiments.

At 110, the sets of sinograms 154 are then used as input for the PCA method (we will refer to the combination of the preprocessing and PCA as Masked Volume Wise PCA, or MVW-PCA). A description of PCA is widely available. In summary, the method finds the dominant eigenvectors of the (estimated) covariance matrix of the data. Its output is a number of eigenvectors (each corresponding to a set of sinograms of the same size as a set 154a) and their corresponding eigenvalues. The eigenvectors with the largest eigenvalue explain the largest variation (over time) in the sets of sinograms 154a . . . 154n. It is possible and advisable to compute only the first few eigenvectors, as the eigenvectors with lowest eigenvalues correspond to noise in the data. These eigenvectors are often called "Principal Components" and labeled PC1, PC2 etc. in order of decreasing eigenvalue. As shown in FIG. 5, the PC1 image represents the first principal component in the exemplary data used in FIG. 4. In this example, the PC1 image illustrates the areas that have the greatest change over time due to motion. For example, the central areas of the objects 160, 162, 164, and 166 which are shown using a substantially solid color (corresponding to values very close to zero) indicate that the values in the original data in this portion of the object did not change substantially over time. Moreover, PC1 shows that there is some motion around the edges of the objects 160, 162, 164, and 166 (shown in FIG. 5) using shaded areas that represent the degree or quantity of motion. For example, PC1 illustrates shaded regions 160a and 160b that represent motion of the object 160. Regions 162a and 162b represent motion of the object 162. Regions 164a and 164b represent motion of the object 164, and regions 166a and 166b represent motion of the object 166. Moreover, the shading indicates the sign of the values in the corresponding elements in PC1. For instance, the shading in 160a indicates positive values, while the shading in 160b indicates negative values. The objects 160, 162, 164, and 166 themselves are shown as a substantially solid color because there is relatively little effect of the motion within the center regions of the objects 160, 162, 164, and 166. Moreover, because there is relatively little effect of motion around the objects 160, 162, 164, and 166, the background 180 is also illustrated as a substantially the same color.

Figure 6:
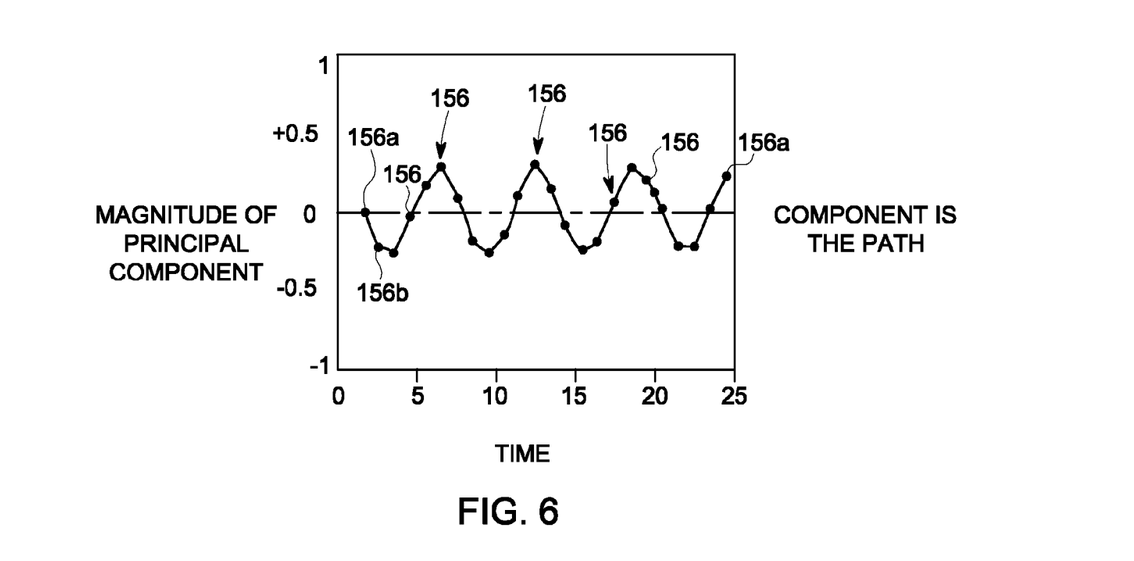
FIG. 6 is exemplary motion information that may be generated in accordance with various embodiments.

Referring again to FIG. 2, at 110, the zero mean information 154 generated for each set of sinograms 150 is utilized to generate one or more weight factors 156, shown in FIG. 6. More specifically, the PCA outputs a single weight factor, signal and/or trace for each principal component analyzed. In this example, the PCA outputs the weight factor 156 corresponding to the first principal component. The weight factor 156 is illustrated as points in FIG. 6, one point for each time frame. In the exemplary embodiment, the weight factor 156 is generated by doing an element-wise multiplication of the values of PC1 with each of the sets of sinograms with the zero mean information 154a . . . 154n, and summing over the set of sinograms, thus obtaining a single number for each set of sinograms 154a, 154b . . . 154n.

More specifically, referring to the image PC1 shown in FIG. 5, PC1 indicates that there is a time change in the emission data that is illustrated by the shading in the regions 160a, 160b, 162a, 162b, 164a, 164b, 166a, and 166. If in a particular time frame, the objects 160, 162, 164, and 166 are in their top-most position, the result of the multiplication of the zero mean information with PC1 will be substantially zero everywhere, except in the regions 160a, 162a, 164a and 166a where it will for instance be positive. Therefore, the value of the weight factor 156 in this time frame will be positive. Conversely, if the objects are in their bottom-most position, the value of the signal will be negative (or in practice have the opposite sign as in the top-most position). Therefore, the value of the weight factor 156 may be a single positive number indicating that a change in magnitude has been observed in a first direction. The value of the weight factor 156 may be a single negative number indicating a negative change in magnitude has been observed in an opposite second direction. The value of the weight factor 156 may be a zero indicating no change with respect to the mean position of the objects. Moreover, the values of the weight factor 156 may be within a range of positive and negative values. For example, a low positive value may indicate relatively small movement of the objects with respect to the mean. Whereas a higher positive value may represent greater movement of the object 16.

Figure 7:
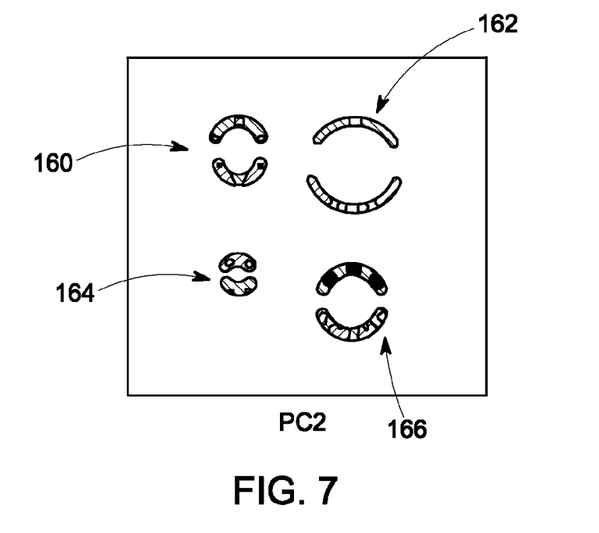
FIG. 7 is another exemplary image representing motion information that may be generated in accordance with various embodiments.

In the exemplary embodiment, the MVW-PCA may be configured to more clearly identify the zero mean information 154. For example, FIG. 7 illustrates an image PC2 that represents a second component that may be output by the PCA. It should be realized that the quantity of PC images generated by the MVW-PCA may be based on the desired accuracy to characterize the zero mean information. For example, the MVW-PCA may utilize only the PC1 image to generate a motion signal that is discussed in more detail below. The motion signals corresponding to different principal components which may be output from the PCA may represent different types of motion, for example, respiratory motion, cardiac motion, body movement, etc. as will be discussed in more detail below.

Figure 8:
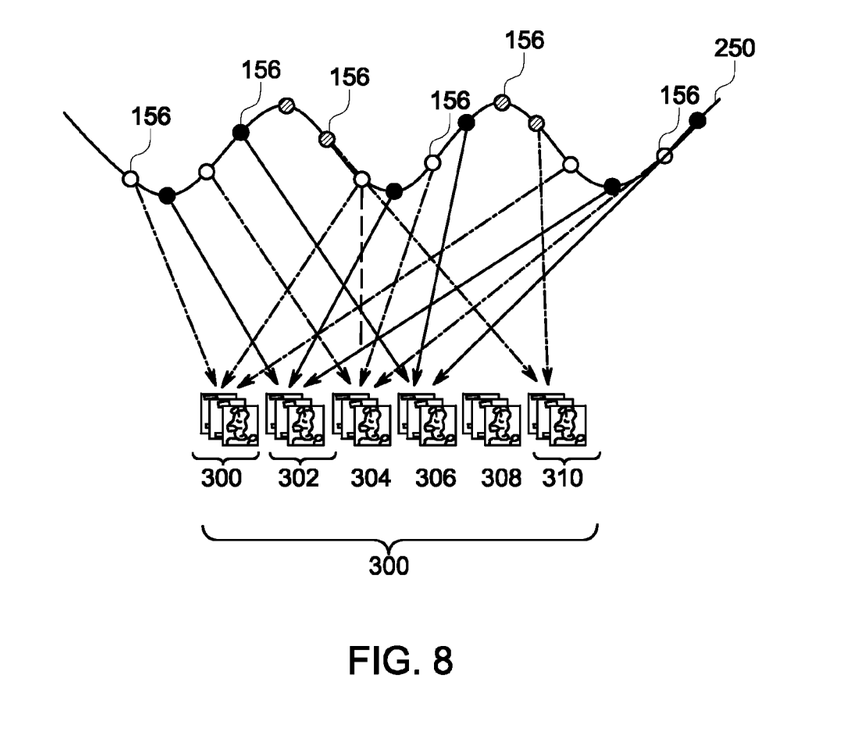
FIG. 8 is an exemplary motion signal that may be generated in accordance with various embodiments.

Referring again to FIG. 2, at 112, the weight factors 156 derived at 110 are utilized to generate a motion signal 250. For example, FIG. 8 illustrates an exemplary motion signal 250 derived using the MVW-PCA wherein the x-axis represents time and the y-axis represents the magnitude of the weight factors 156 derived at 110 for each set of sinograms 150. In the exemplary embodiment, the weight factors 156 are derived in a time sequential manner for each of the sets of sinograms 150. For example, the MVW-PCA derives a weight factor 156a for the set of sinograms 150a, which in the exemplary embodiment, is the first sinogram generated during the scan. The MVW-PCA then derives a weight factor 156b for the second set of sinograms 150b, and derives a weight factor 156n for the last set of sinograms 150n acquired in the scanning procedure. As shown in FIG. 8, the plurality of weight factors 156 are arranged in a time sequential manner and a line has been drawn through the points representing the weight factors 156. From the weight factors 156, the motion signal 250 is derived. In one embodiment, the motion signal 250 is substantially the same as the weight factors 156. In another embodiment, the motion signal 250 is obtained by filtering the weight factors 156, to for example, reduce noise.

Figure 9:
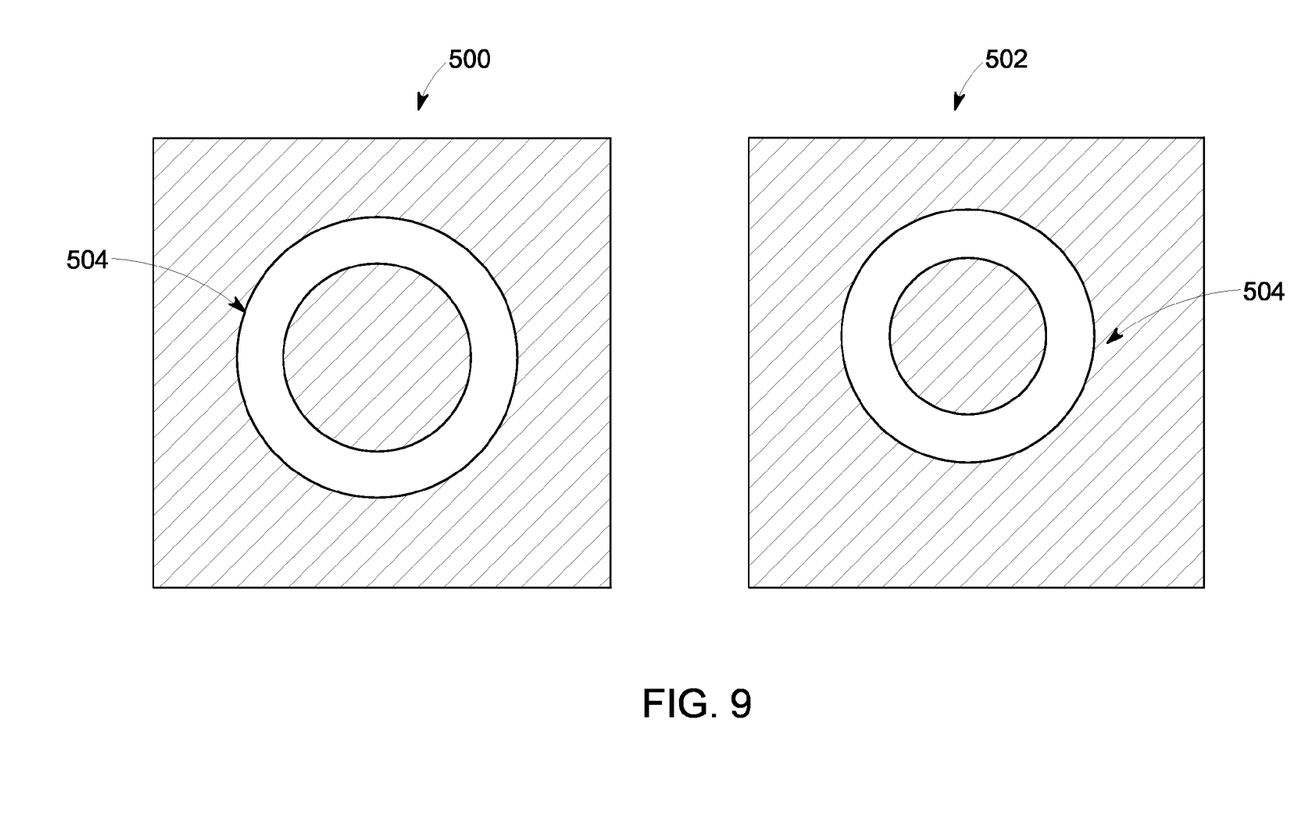
FIG. 9 are exemplary images that may be generated in accordance with various embodiments.

At 114, the emission dataset 14, e.g. the sinograms 150, is sorted into a plurality of bins 300 using the motion signal 250 (shown in FIG. 8). For example, FIG. 8 illustrates the exemplary motion signal 250 that is utilized to map the sinograms 150 into a plurality of bins 300. Moreover, FIG. 9 illustrates a plurality of bins numbered 300 ... 310, i.e. n=6 bins. Thus, in the exemplary embodiment, the sinograms 150 are sorted into the six bins 300 numbered 300, 302, 304, 306, 308, and 310. However, it should be realized that the quantity of bins illustrated in FIG. 8 is exemplary, and that during operation, fewer than six bins or more than six bins may be utilized. As such, each bin 300, 302, 304, 306, 308, and 310 includes approximately ⅙ of the total information in the imaging dataset 14.

For example, assuming that the total length of the scan performed at 102 to acquire emission data is three minutes. Moreover, assuming that the imaging dataset 14 is sorted into six bins, wherein each respective bin includes approximately 30 seconds of information. In the exemplary embodiment, the sinograms 150 are sorted into a respective bin based on the motion signal 250 described above. More specifically, the sinograms 150 are sorted into a specific bin based on the value of the motion signal 250 derived as discussed above. Accordingly, in the exemplary embodiment, each bin includes emission data that represents the objects 160, 162, 164, and 166 in the same approximate spatial position during the scanning procedure. For example, the bin 300 may include information that represents the object 160 acquired at the beginning of a respiration phase, and the bin 310 may include imaging data acquired at the end of the respiration phase. Moreover, each intervening bin, e.g. bins 302, 304, 306, and 308 may include imaging data that represents a motion state between inspiration and expiration. Each of the bins 300, 302, 304, 306, 308, and 310 is adapted to receive imaging data that is acquired over a plurality of breathing cycles. Moreover, each of the bins 300, 302, 304, 306, 308, and 310 is adapted to receive imaging data that represents approximately the same point in the patient's breathing cycle. Accordingly, each of the bins 300, 302, 304, 306, 308, and 310 include imaging data representing a certain motion state of the patient 16. In the exemplary embodiment, the information acquired from the motion signal 250 is utilized to divide the imaging data 14 into six substantially equal portions and store the substantially equal portions in a respective bin 300, 302, 304, 306, 308, and 310. Thus, at the conclusion of the gating process at 114 each of the six bins 300, 302, 304, 306, 308, and 310 includes emission data associated with the same motion characteristics.

In the exemplary embodiment, after the emission data is sorted into bins, the plurality of bins 300, 302, 304, 306, 308, and 310 may be reconstructed into images representing emission activity distribution and then spatially registered. For example, in one embodiment, the bin 300 may be selected as a reference bin and the bins 302, 304, 306, 308, and 310 may be registered to the reference bin 300. The bins 02, 304, 306, 308, and 310 may be registered to the reference bin 300 using either a rigid or non-rigid registration. The rigid and non-rigid registrations may be performed manually by the operator or automatically by the processor 30. It should be realized, that registration may not be required in certain areas where there is little or no motion. The motion information can be used to adjust the cost function in the registration process. In general, the motion information may be utilized to identify areas that are affected by motion or not affected by motion improve the registration process.

In the exemplary embodiment, performing a non-rigid registration includes transforming the information within the bins 302, 304, 306, 308, and 310 in three-dimensional (3D) space to align the information within the bins 302, 304, 306, 308, and 310 to the reference bin 300. For example, the images in the bin 302 may be slighted tilted with respect to the images in the reference bin 300. Accordingly, the images within the bin 302 are tilted to align the images with the images in the reference bin 300. The remaining bins 304, 306, 308 and 310 are also realigned to substantially match the images in the reference bin 300. In operation, the rigid registration process may be implemented by selecting anatomical or other features/points/landmarks and the images aligned using these feature or points along with detected edges or borders within the images. Alternatively, different markers may be used to identify known anatomical locations. The rigid registration also may be based on curved contours, for example, of bones within the image. The rigid registration may also be volume based or surface based. However, it should be appreciated that any rigid registration process may be performed that includes optimizing or calculating a certain comparable criteria or similarity measure.

In another embodiment, a non-rigid registration procedure may be utilized to perform the motion correction on the information within the bins 300, 302, 304, 306, 308, and 310. In operation, the non-rigid registration or elastic registration includes non-rigid transformations. These non-rigid transformations allow local warping of image features and provide registrations that account for local deformations.

Non-rigid transformation approaches include, for example, polynomial warping, interpolation of smooth basis functions (thin-plate splines and wavelets), and physical continuum models (viscous fluid models and large deformation diffeomorphisms). The non-rigid registration is performed using the information sorted in the bins 300, 302, 304, 306, 308, and 310. The non-rigid registration may include, for example, warping of points or landmarks and providing a best fit along a contour with interpolation and correlation of the points or landmarks. Alternatively, a blending process may be performed that compares image voxels and blends corresponding regions. In general, the local non-rigid registration includes any type of elastic deformation model that allows for variations or movements in the different image sets.

Referring again to FIG. 2, at 116, the 2D images stored in the bins 300, 302, 304, 306, 308, and 310, i.e., the motion corrected images, are averaged together to generate a single motion corrected image.

Figure 10:
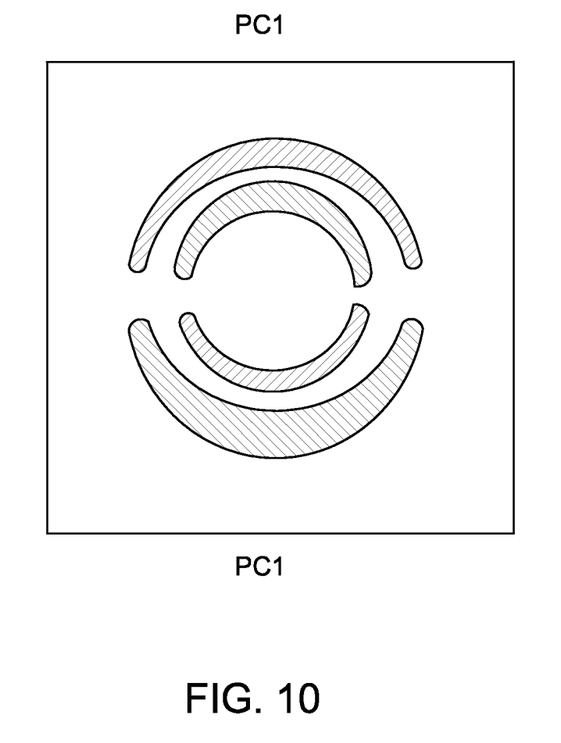
FIG. 10 is another exemplary image representing motion information that may be generated in accordance with various embodiments.
Figure 11:
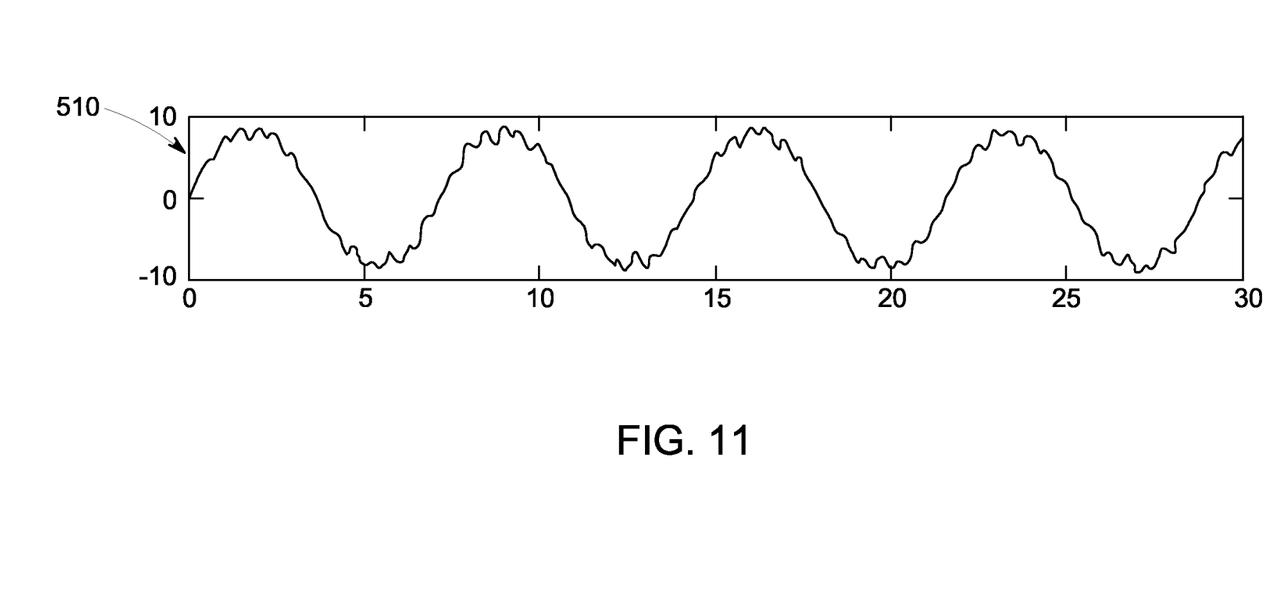
FIG. 11 is exemplary motion information that may be generated in accordance with various embodiments.
Figure 12:
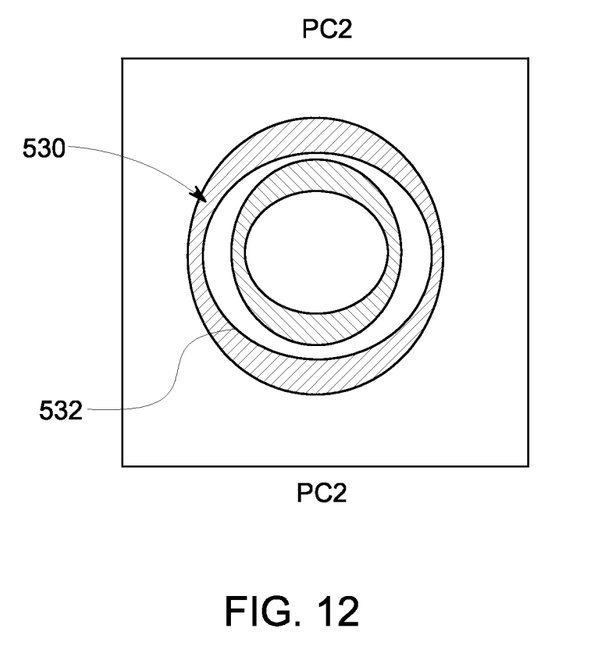
FIG. 12 is another exemplary image representing motion information that may be generated in accordance with various embodiments.
Figure 13:
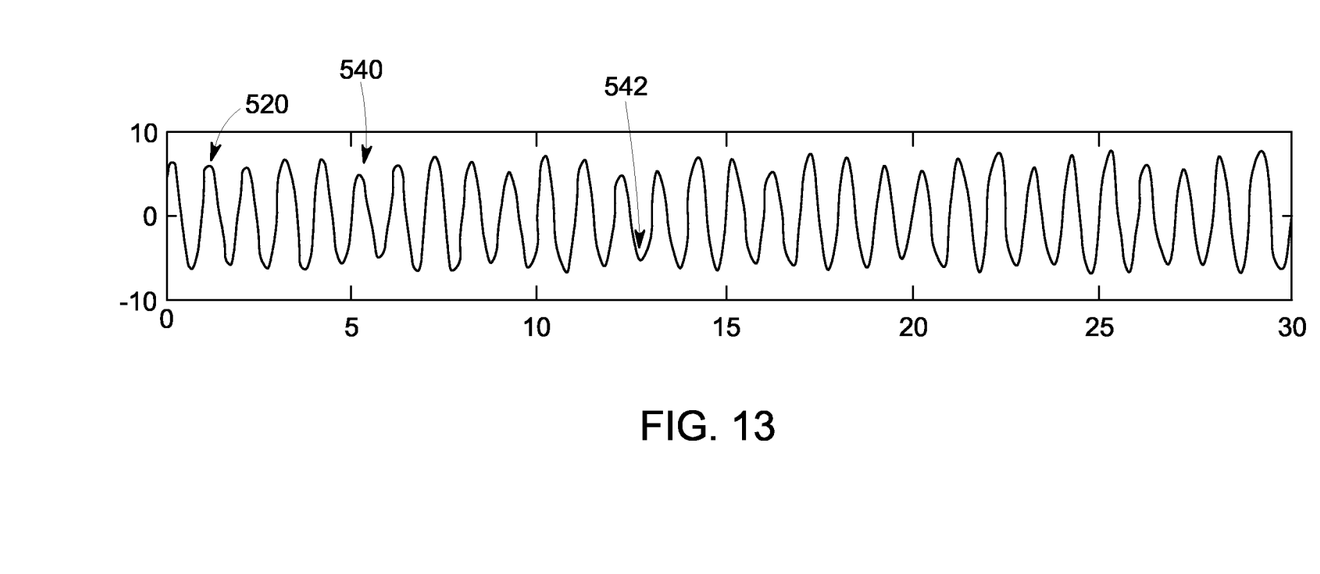
FIG. 13 is exemplary motion information that may be generated in accordance with various embodiments.

In another embodiment, MVW-PCA is used to construct multiple motion signals corresponding to different types of movement, such as respiratory, cardiac and/or whole body movement. For example, FIG. 9 illustrates two time frames 500 and 502 acquired by scanning an exemplary uniform object 504, similar to the myocardium, where in this case the motion represents a contraction/expansion and a translation in vertical direction at a different (slower) rate. FIG. 10 illustrates the first principal component PC1 obtained in this example from the object 504 shown in FIG. 9. MVW-PCA shows similar features as in FIG. 5. FIG. 11 illustrates a weight factor 510 corresponding to this component as constructed in the previous embodiment. In this example, it is mostly determined by the translation (or respiratory movement). FIG. 12 illustrates the second component PC2, and a corresponding weight factor 520 is shown in FIG. 13. In this example, PC2 is mostly determined by the contractive (or cardiac) movement. More specifically, a region 530, shown in FIG. 12, has substantially positive numbers while a region 532 has substantially negative numbers. Therefore, and referring again to FIG. 13, when the annulus has a large radius in a particular time frame, the weight factor 520 constructed from PC2 will be substantially positive as shown at 540. Similarly, when the annulus has a small radius, the signal will be substantially negative as shown at 542.

Similarly to the previous embodiment, the weight factors are then used as input to a dual-gating module to bin the emission data where each gate corresponds to a particular respiratory and cardiac state. For example, if 6 respiratory states are identified and 3 cardiac states, a total of 18 bins will be used, where the signal 510 determines the respiratory state and the weight factor 520 the cardiac state. In the exemplary embodiment, the binned emission data is then reconstructed and the resulting images are registered to each other. The registration algorithms can take the different types of motion into account and for instance estimate the combined motion of translation and contraction.

In a further embodiment, the principal components and/or their corresponding signals are analyzed to identify the type of motion to allow further processing depending on the application. As an example, the application might correct for respiratory motion, but keep the cardiac gates to determine the ejection fraction. The identification process uses known features of the respective movement. For instance, respiratory motion occurs mostly in the feet-to-head direction, and therefore the corresponding principal component will have mostly values of the opposite sign at the top and bottom of a structure as opposed to contractive motion. In one embodiment, the approximate center of the heart is determined and radial profiles are constructed from the principal components. If the profiles are substantially the same in top and bottom directions, the PC is labeled as corresponding to cardiac and vice versa. Alternatively or in addition, a frequency analysis is performed on the signals corresponding to the principal components. If the dominant frequency is in a range of for instance 1 to 2 cycles per second, the PC is labeled as corresponding to cardiac beating, while a range of for instance $\frac{1}{10}$ to $\frac{1}{2}$ cycles per second is labeled as corresponding to respiratory movement. Similarly, very slow movement or very sudden movement can be labeled as corresponding to whole body movement. In this embodiment, it might be advantageous to, after identification, process the PCs or their signals according to their known features to reduce noise and/or to remove interference between the different types of motion. In the given example, the signal 510, once labeled as mostly respiratory, can be filtered with a mid-pass filter to remove frequencies not corresponding to respiration, and similar appropriate filters for the other signals. For some applications, it might be advantageous to use the filtered signals to determine the gating.

Moreover, alternative multivariate data analysis techniques may be utilized to extract the components. Such multivariate data analysis techniques may include, for example, Independent Component Analysis (ICA) and regularized Principal Component Analysis (rPCA), although it should be realized that other analysis techniques may be utilized, many of which use PCA as an initial step. Some of these techniques allow the usage of prior information about the expected motion patterns which can be advantageous in noisy situations. As a simple example, the sets of sinograms 150 can be first filtered spatially and/or temporally to remove unwanted frequencies. For instance, if only respiratory movement needs to be detected, a temporal mid-pass filter can be applied to the data before using PCA. In the exemplary embodiment, a Masked Volume Wise Principal Component Analysis (MVW-PCA) statistical technique is utilized. In operation, the MVW-PCA analyzes the emission dataset 14 to find the clinically relevant components. In this case, the MVW-PCA is utilized to identify motion related components. More specifically, MVW-PCA is a mathematical algorithm that is utilized to separate the motion information from the diagnostic information and noise. In the exemplary embodiment, the MVW-PCA is implemented as instructions that may be stored on, for example, the motion characterization module 50 and/or the memory device 20.

Figure 14:
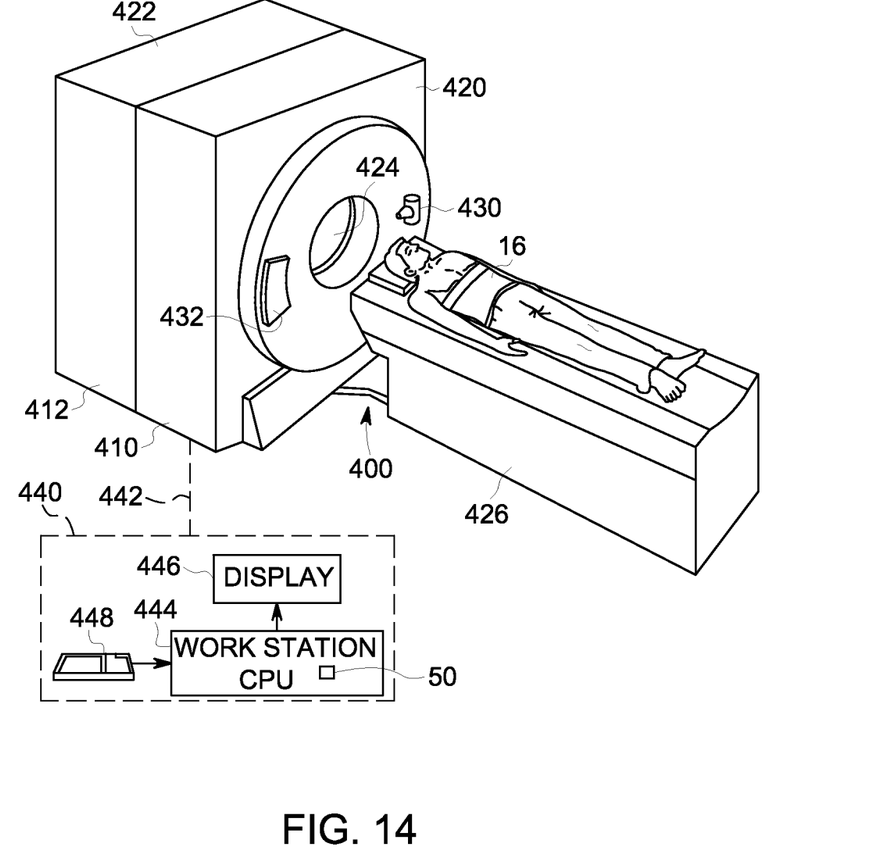
FIG. 14 is a pictorial illustration of an exemplary imaging system formed in accordance with various embodiments.

Various embodiments described herein may provide a multi-modality imaging system 400 as shown in FIG. 14. The multi-modality imaging system 400 may be any type imaging system, for example, different types of medical imaging systems, such as the Positron Emission Tomography (PET) 10 shown in FIG. 1, a Single Photon Emission Computed Tomography (SPECT), a Computed Tomography (CT), an ultrasound system, Magnetic Resonance Imaging (MRI) or any other system capable of generating diagnostic images. The various embodiments are not limited to multi-modality medical imaging systems, but may be used on a single modality medical imaging system such as a stand-alone PET imaging system, a stand-alone CT imaging system, an Magnetic Resonance Imaging (MRI), and a Photon Emission Computed Tomography (SPECT), for example. Moreover, the various embodiments are not limited to medical imaging systems for imaging human subjects, but may include veterinary or non-medical systems for imaging non-human objects, etc.

Referring to FIG. 14, the multi-modality imaging system 400 includes a first modality unit 410 and a second modality unit 412. The two modality units enable the multi-modality imaging system 400 to scan an object or patient 16 in a first modality using the first modality unit 410 and to scan the patient 16 in a second modality using the second modality unit 412. The multi-modality imaging system 400 allows for multiple scans in different modalities to facilitate an increased diagnostic capability over single modality systems. In one embodiment, the multi-modality imaging system 400 is a CT/PET imaging system 400, e.g. the first modality 410 is a CT imaging system and the second modality 412 is the PET imaging system 10. The imaging system 400 is shown as including a gantry 420 that is associated with the CT imaging system 410 and a gantry 422 that is associated with the PET imaging system 10. During operation, the patient 16 is positioned within a central opening 424, defined through the imaging system 400, using, for example, a motorized table 426.

The gantry 420 includes an x-ray source 430 that projects a beam of x-rays toward a detector array 432 on the opposite side of the gantry 420. The detector array 432 is formed by a plurality of detector rows (not shown) including a plurality of detector elements which together sense the projected x-rays that pass through the patient 16. Each detector element produces an electrical signal that represents the intensity of an impinging x-ray beam and hence allows estimation of the attenuation of the beam as the beam passes through the patient 16. During a scan to acquire x-ray attenuation data, the gantry 420 and the components mounted thereon rotate about a center of rotation. Additionally, the PET imaging system includes a detector (not shown) that is configured to acquire emission data.

During operation, the motorized table 426 moves the patient 16 into the central opening 424 of the gantry 420 and/or the gantry 422 in response to one or more commands received from the operator workstation 440. The workstation 440 then operates the first and second modalities 410 and 412 to both scan the patient 16 and acquire attenuation and/or emission data of the patient 16. The workstation 440 may be embodied as a personal computer (PC) that is positioned near the imaging system 400 and hard-wired to the imaging system 440 via a communication link 442. The workstation 440 may also be embodied as a portable computer such as a laptop computer or a hand-held computer that transmits information to, and receives information from, the imaging system 400. Optionally, the communication link 442 may be a wireless communication link that enables information to be transmitted to or from the workstation 440 to the imaging system 400 wirelessly. In operation, the workstation 440 is configured to control the operation of the imaging system 400 in real-time. The workstation 440 is also programmed to perform medical image diagnostic acquisition and reconstruction processes described herein. More specifically, the workstation 444 may include the motion characterization module 50 that is adapted to identify motion within the 4D dataset 14 and utilize the identified motion to partition the 4D dataset 14 into a plurality of bins which are then used to reconstruct an image of the patient 16 as is discussed in more detail above.

The operator workstation 440 includes a central processing unit (CPU) or computer 444, a display 446, and an input device 448. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 444 executes a set of instructions that are stored in one or more storage elements or memories, in order to process information received from the first and second modalities 410 and 412. The storage elements may also store data or other information as desired or needed. The storage element may be in the form of an information source or a physical memory element located within the computer 444.

The set of instructions may include various commands that instruct the computer 444 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The computer 444 connects to the communication link 442 and receives inputs, e.g., user commands, from the input device 448. The input device 448 may be, for example, a keyboard, mouse, a touch-screen panel, and/or a voice recognition system, etc. Through the input device 448 and associated control panel switches, the operator can control the operation of the CT imaging system 410 and the PET imaging system 10 and the positioning of the patient 16 for a scan. Similarly, the operator can control the display of the resulting image on the display 446 and can perform image-enhancement functions using programs executed by the computer 444.

A technical effect of some of the various embodiments described herein is to improve image quality and to compensate for respiratory motion, cardiac motion, patient motion, etc. More specifically, MVW-PCA may be utilized to improve the detection and visualization of significant motion changes and to sort the image data into bins based on the detected changes in order to improve image quality and capture the motion in order to reduce the upcoming artifact, and improve the detection of various objects, such as for example, tumors. The image data may be acquired using a PET imaging system, a SPECT imaging system, an MRI imaging system, an ultrasound imaging system, and/or an MRI imaging system, for example.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for reducing, in an image, motion related imaging artifacts, said method comprising:
   obtaining an image dataset of a region of interest;
   generating a plurality of intermediate images using the image dataset;
   applying a multivariate data analysis technique to the plurality of the intermediate images to generate motion information;
   sorting the intermediate images into a plurality of bins based on the motion information; and
   generating an image of the region of interest using at least one of the plurality of bins.

2. The method of claim 1, wherein obtaining the image dataset further comprises obtaining at least one of a four-dimensional (4D) Positron Emission Tomography (PET) emission dataset, a 4D Single Photon Emission Computed Tomography (SPECT) emission dataset, or a 4D Computed Tomography (CT) dataset.

3. The method of claim 1, wherein applying a multivariate data analysis technique further comprises applying a Masked Volume Wise Principal Component Analysis (MVW-PCA) to the plurality of intermediate images to generate the motion information.

4. The method of claim 1, further comprising:
   performing the multivariate data analysis technique of the plurality of intermediate images to generate a plurality of weight factors; and
   sorting the intermediate images into the plurality of bins based on the plurality of weight factors.

5. The method of claim 1, further comprising:
   applying the multivariate data analysis technique of the intermediate images to a plurality of weight factors;
   generating a motion signal using the plurality of weight factors; and
   sorting the intermediate images into the plurality of bins based on the motion signal.

6. The method of claim 5, wherein generating further comprises generating a motion signal using a plurality of filtered weight factors.

7. The method of claim 1, further comprising:
   applying the multivariate data analysis technique of intermediate images to generate a single weight factor for each intermediate image in the plurality of intermediate images; and
   sorting the intermediate images into the plurality of bins based on a value of each of the weight factors.

8. The method of claim 1, further comprising sorting the plurality of bins using a dual-gating technique.

9. The method of claim 1, further comprising performing the multivariate data analysis technique to the plurality of intermediate images to generate motion information of different types of movement, said different types of movement including at least one of respiratory movement, cardiac movement or whole body movement.

10. The method of claim 9, further comprising identifying different types of motion using a frequency analysis of the motion information.

11. The method of claim 1, further comprising performing at least one of a rigid registration or a non-rigid registration on the generated image.

12. A medical imaging system comprising a scanner and a computer operationally coupled to the scanner, wherein the computer is programmed to:
   acquire an imaging dataset of an object using the scanner;
   generate a plurality of intermediate images using the image dataset;
   apply a multivariate data analysis technique to the plurality of intermediate images to generate motion information;
   sort the intermediate images into a plurality of bins based on the motion information; and
   generate an image of the region of interest using at least one of the plurality of bins.

13. The medical imaging system of claim 12, wherein the computer is further programmed to obtain at least one of a four-dimensional (4D) Positron Emission Tomography (PET) emission dataset and a 4D Single Photon Emission Computed Tomography (SPECT) emission dataset, or a 4D Computed Tomography (CT) dataset.

14. The medical imaging system of claim 12, wherein to perform the multivariate data analysis technique the computer is further programmed to perform a Masked Volume Wise Principal Component Analysis (MVW-PCA) of the plurality of intermediate images to generate the motion information.

15. The medical imaging system of claim 12, wherein the computer is further programmed to:
 identify different types of motion using a frequency analysis of the motion information.

16. The medical imaging system of claim 12, wherein the computer is further programmed to:
 apply the multivariate data analysis technique of the plurality of intermediate images to generate a plurality of weight factors; and
 sort the intermediate images into a plurality of bins based on the weight factors.

17. The medical imaging system of claim 12, wherein the computer is further programmed to:
 apply the multivariate data analysis technique of the plurality of intermediate images to generate a plurality of weight factors;
 generate a motion signal using the plurality of weight factors; and
 sort the intermediate images into a plurality of bins based on the motion signal.

18. A non-transitory computer readable medium encoded with a program programmed to instruct a computer to:
 acquire an imaging dataset of an object using the scanner;
 generate a plurality of intermediate images using the image dataset;
 apply a multivariate data analysis technique to the plurality of intermediate images to generate motion information;
 sort the intermediate images into a plurality of bins based on the motion information; and
 generate an image of the region of interest using at least one of the plurality of bins.

19. A computer readable medium in accordance with claim 18, wherein to apply the multivariate data analysis technique said computer readable medium is further programmed to instruct a computer to perform a Masked Volume Wise Principal Component Analysis (MVW-PCA) of the plurality of intermediate images to generate the motion information.

20. A computer readable medium in accordance with claim 18, said computer readable medium is further programmed to instruct a computer to:
 apply the multivariate data analysis technique of the plurality of intermediate images to generate a plurality of weight factors; and
 sort the intermediate images into the plurality of bins based on the weight factors.

\* \* \* \* \*